United States Patent
Sun et al.

(10) Patent No.: US 7,480,530 B2
(45) Date of Patent: Jan. 20, 2009

(54) DEVICE FOR TREATMENT OF BARRIER MEMBRANES

(75) Inventors: Ying Sun, Belle Mead, NJ (US); Jue-Chen Liu, Belle Mead, NJ (US); Jeffrey M. Wu, Warrington, PA (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/609,727

(22) Filed: Jun. 30, 2003

(65) Prior Publication Data

US 2004/0267169 A1    Dec. 30, 2004

(51) Int. Cl.
*A61N 1/30* (2006.01)
*A61M 31/00* (2006.01)

(52) U.S. Cl. .......................... 604/20; 604/501
(58) Field of Classification Search .................. 604/20, 604/19, 61, 501, 890.1–892.1, 500; 424/448–449; 607/120, 152, 289, 39, 43, 20
See application file for complete search history.

(56) References Cited

U.S. PATENT DOCUMENTS

| | | | |
|---|---|---|---|
| 4,305,390 A | 12/1981 | Swartz | |
| 4,372,296 A | 2/1983 | Fahim | |
| 4,406,658 A | 9/1983 | Lattin et al. | |
| 4,474,570 A | 10/1984 | Ariura et al. | |
| 4,767,401 A | 8/1988 | Seiderman | |
| 4,842,577 A | 6/1989 | Konno et al. | |
| 4,956,184 A | 9/1990 | Kross | |
| 4,957,480 A | 9/1990 | Morenings | |
| 4,979,938 A | 12/1990 | Stephen et al. | |
| 5,042,975 A | 8/1991 | Chien et al. | |
| 5,147,297 A | 9/1992 | Myers et al. | |
| 5,162,043 A | 11/1992 | Lew et al. | |
| 5,298,017 A | 3/1994 | Theeuwes et al. | |
| 5,314,502 A | 5/1994 | McNichols et al. | |
| 5,326,341 A | 7/1994 | Lew et al. | |
| 5,338,412 A | 8/1994 | Burk et al. | |
| 5,356,632 A * | 10/1994 | Gross et al. | 424/449 |
| 5,380,272 A | 1/1995 | Gross | |
| 5,384,134 A | 1/1995 | Kross et al. | |
| 5,387,189 A | 2/1995 | Gory et al. | |
| 5,405,317 A | 4/1995 | Myers et al. | |
| 5,415,628 A | 5/1995 | Untereker et al. | |

(Continued)

FOREIGN PATENT DOCUMENTS

EP    0 337 642 A    10/1989

(Continued)

OTHER PUBLICATIONS

Data sheet ionto Patch publicly available prior to Jun. 30, 2003.

(Continued)

*Primary Examiner*—Manuel A Mendez

(57) ABSTRACT

The present invention features a device having a barrier membrane contacting surface, the device containing: a power source; a first conductive electrode; a second conductive electrode; and a carrier; wherein the power source is in electric communication with the first conductive electrode and the second conductive electrode, wherein the first conductive electrode and the second conductive electrode are in ionic communication with the carrier, and wherein the carrier is in communication with the barrier membrane contacting surface.

26 Claims, 6 Drawing Sheets

U.S. PATENT DOCUMENTS

| | | | |
|---|---|---|---|
| 5,428,185 A | 6/1995 | Kunimoto et al. | |
| 5,443,441 A | 8/1995 | De Claviere | |
| 5,466,217 A | 11/1995 | Myers et al. | |
| 5,470,349 A | 11/1995 | Kleditsch et al. | |
| 5,624,415 A | 4/1997 | Ledger et al. | |
| 5,624,425 A | 4/1997 | Gray et al. | |
| 5,637,084 A | 6/1997 | Kontturi et al. | |
| 5,678,545 A | 10/1997 | Stratbucker | |
| 5,685,837 A | 11/1997 | Horstmann | |
| 5,688,233 A | 11/1997 | Hofmann et al. | |
| 5,817,044 A | 10/1998 | Evers et al. | |
| 5,855,570 A | 1/1999 | Scherson et al. | |
| 5,897,522 A | 4/1999 | Nitzan | |
| 5,928,185 A * | 7/1999 | Muller et al. | 604/20 |
| 5,935,598 A * | 8/1999 | Sage et al. | 424/449 |
| 5,955,017 A | 9/1999 | Foffano et al. | |
| 5,955,067 A | 9/1999 | Oge et al. | |
| 5,961,483 A * | 10/1999 | Sage et al. | 604/20 |
| 5,993,435 A | 11/1999 | Haak et al. | |
| 6,004,309 A * | 12/1999 | Phipps | 604/501 |
| 6,078,842 A | 6/2000 | Gross et al. | |
| 6,104,950 A | 8/2000 | Higo et al. | |
| 6,157,858 A | 12/2000 | Gross et al. | |
| 6,169,920 B1 | 1/2001 | Haak et al. | |
| 6,185,453 B1 * | 2/2001 | Hussain et al. | 604/21 |
| 6,231,830 B1 | 5/2001 | Madray | |
| 6,238,381 B1 | 5/2001 | Tapper | |
| RE37,263 E | 7/2001 | Kross et al. | |
| 6,275,372 B1 | 8/2001 | Vassallo et al. | |
| 6,289,241 B1 | 9/2001 | Phipps | |
| 6,302,874 B1 | 10/2001 | Zhang et al. | |
| 6,306,384 B1 | 10/2001 | Lahanas et al. | |
| 6,317,629 B1 | 11/2001 | Haak et al. | |
| 6,385,487 B1 | 5/2002 | Henley | |
| 6,421,561 B1 | 7/2002 | Morris | |
| 6,424,862 B1 | 7/2002 | Brown, III et al. | |
| 6,443,978 B1 | 9/2002 | Zharov | |
| 6,455,065 B1 | 9/2002 | Hymes | |
| 6,488,965 B1 | 12/2002 | Karageozian | |
| 6,494,900 B1 | 12/2002 | Salansky et al. | |
| 6,495,158 B1 | 12/2002 | Buseman et al. | |
| 6,522,918 B1 | 2/2003 | Crisp et al. | |
| 6,544,401 B1 | 4/2003 | Colic | |
| 6,552,895 B1 | 4/2003 | Vassallo et al. | |
| 6,560,483 B1 | 5/2003 | Kumar et al. | |
| 6,582,416 B2 | 6/2003 | Tapper | |
| 6,584,349 B1 | 6/2003 | Sage, Jr. et al. | |
| 6,631,294 B2 | 10/2003 | Andino et al. | |
| 6,653,014 B2 | 11/2003 | Anderson et al. | |
| 6,654,635 B1 | 11/2003 | Koga et al. | |
| 6,708,050 B2 | 3/2004 | Carim | |
| 6,735,470 B2 | 5/2004 | Henley et al. | |
| 6,738,662 B1 | 5/2004 | Frank | |
| 6,745,071 B1 | 6/2004 | Anderson et al. | |
| 6,766,202 B2 | 7/2004 | Underwood et al. | |
| 6,775,570 B2 * | 8/2004 | Joshi | 604/20 |
| 6,821,281 B2 | 11/2004 | Sherman et al. | |
| 6,855,117 B2 | 2/2005 | Skover | |
| 6,866,856 B2 | 3/2005 | Lu et al. | |
| 2002/0099320 A1 | 7/2002 | Beck | |
| 2002/0173833 A1 | 11/2002 | Korman et al. | |
| 2002/0183685 A1 | 12/2002 | Crawford et al. | |
| 2002/0188241 A1 | 12/2002 | Morris et al. | |
| 2003/0023270 A1 | 1/2003 | Danz et al. | |
| 2003/0028170 A1 | 2/2003 | Anderson et al. | |
| 2003/0059673 A1 | 3/2003 | Langan et al. | |
| 2003/0149393 A1 | 8/2003 | Joshi | |
| 2003/0176832 A1 | 9/2003 | Rossi | |
| 2003/0216783 A1 | 11/2003 | Lehtoluoto | |
| 2004/0006374 A1 | 1/2004 | Wieland | |
| 2004/0020371 A1 | 2/2004 | Patenotre et al. | |
| 2004/0043062 A1 | 3/2004 | Sun | |
| 2004/0167460 A1 | 8/2004 | Anderson et al. | |
| 2004/0167461 A1 | 8/2004 | Nitzan et al. | |
| 2004/0265395 A1 | 12/2004 | Sun et al. | |
| 2004/0267189 A1 | 12/2004 | Marr et al. | |
| 2004/0267190 A1 | 12/2004 | Tamarkin et al. | |
| 2004/0267231 A1 | 12/2004 | Sun et al. | |
| 2004/0267232 A1 | 12/2004 | Sun et al. | |
| 2004/0267236 A1 | 12/2004 | Sun et al. | |
| 2004/0267237 A1 | 12/2004 | Sun et al. | |
| 2005/0004508 A1 | 1/2005 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 | 1/2005 | Sun et al. | |
| 2005/0015042 A1 | 1/2005 | Sun et al. | |
| 2005/0148996 A1 | 7/2005 | Sun et al. | |

FOREIGN PATENT DOCUMENTS

| | | | |
|---|---|---|---|
| EP | 0532451 A1 | 3/1993 | |
| EP | 1008365 A1 | 6/2000 | |
| EP | 1484012 A1 | 12/2004 | |
| JP | 03080874 A | 4/1991 | |
| JP | 10024108 A | 1/1998 | |
| WO | WO93/00959 A1 | 1/1993 | |
| WO | WO94/11058 A1 | 5/1994 | |
| WO | WO94/17853 A1 | 8/1994 | |
| WO | WO98/14237 A1 | 4/1998 | |
| WO | WO99/56819 A1 | 11/1999 | |
| WO | WO00/12173 A1 | 3/2000 | |
| WO | WO97/06847 A1 | 8/2000 | |
| WO | WO00/62856 A1 | 10/2000 | |
| WO | WO00/62857 A1 | 10/2000 | |
| WO | WO00/74772 A1 | 12/2000 | |
| WO | WO01/80945 A1 | 11/2001 | |
| WO | WO03/082095 A1 | 10/2002 | |
| WO | WO02/098502 A2 | 12/2002 | |
| WO | WO99/43382 A1 | 11/2003 | |
| WO | WO2005/004984 A1 | 1/2005 | |

OTHER PUBLICATIONS

Electrochemistry Handbook Table 14.1, McGraw Hill Inc. 1995 pp. 14.3-14.16.

G. Stux, B. Berman, B. Pomeranz, Basics of Acupuncture, Springer 2003 pp. 306-309.

R. Davis, Can Acupuncture Punch Up Your Appearance? Wall Street Journal Health article published Dec. 21, 2004. pp. D7.

P. Spacciapoli, D. Buxton, D. Rothstein, P. Friden, Antimicrobial activity of silver nitrate against periodoental pathogens, Journal of Peridontal Research, 2001, 36:108-113.

International Search Report for PCT/US2004/020382 dated Nov. 4, 2004 for publication No. WO2005/004979.

* cited by examiner

DEVICE FOR TREATMENT OF BARRIER MEMBRANES

FIELD OF THE INVENTION

The present invention relates to a device for application to a barrier membrane.

BACKGROUND OF THE INVENTION

Transdermal devices have been widely prescribed for decades in the treatment of is systemic diseases and local conditions. During passive transdermal delivery, an active agent is delivered into a mammal by using a concentration gradient across a barrier membrane (e.g., through passive diffusion through skin). For example, a patch containing the drug in high concentration is affixed to the skin of a patient.

Electricity may be employed to facilitate drug transport across the skin barrier. In electricity-assisted devices, an electric potential (voltage) is applied to the membrane to facilitate drug transport. In transdermal iontophoresis, an ionized drug migrates into the skin driven by an applied electric potential gradient. Anionic drugs are delivered into the skin under the cathode (negatively charged electrode), while cationic drugs are delivered under the anode (positively charged electrode). Iontophoresis enables enhanced as well as better control of permeation rate of the ionic species into the skin.

The most common design of an iontophoresis device includes a power source (e.g., a battery), an electric control mechanism, and two separate conductive electrodes. Each conductive electrode is in contact with a separate electrolyte composition (with or without an active agent). The electrolyte or ionic active composition is generally either an aqueous solution contained in a liquid chamber or a semi-solid. The assembly of the conductive electrode and electrolyte composition is often referred to as "an electrode assembly" or simply "an electrode." The two electrode assemblies are usually affixed to the skin separated by electric insulation between them.

Alternatively, the two electrode assemblies may be constructed into a single iontophoresis device with an electric insulating material built between the two electrode assemblies for electrical isolation to prevent shorting current. An example of such an iontophoresis device is disclosed in U.S. Pat. No. 5,387,189.

In another variation of the common iontophoresis device designs, the electrolyte composition in one of the two electrode assemblies is eliminated, and the conductive electrode is placed directly in contact with the skin to complete the electric circuit. An example of such iontophoresis device is disclosed in U.S. Pat. No. 6,385,487.

During a typical iontophoresis operation (mono-polar operation), one of the two electrodes (i.e., active electrode) drives the active agent into the skin. The other electrode (i.e., disperse electrode) serves to close the electrical circuit through the skin. Sometimes, a second active agent of opposite electric charge can be placed into electrolyte composition in contact with the second electrode, thus, being delivered into the skin under the second electrode. Alternatively, the electric polarity of the first and second electrodes can be reversed periodically to drive ionic species under both electrodes (bi-polar operation). A bi-polar iontophoresis device for transdermal drug delivery is disclosed U.S. Pat. No. 4,406,658.

Acne and rosacea are major diseases of the skin associated with sebaceous follicles on the skin. There are many treatments, but no cures for acne or rosacea. Such treatments for acne include antibiotics (which kill or inhibit growth of *p. acnes* bacteria which play a role in acne), retinoids such as tretinoin and isotetinoin, antimicrobials such as benzoyl peroxide, and keratolytic agents such as salicylic acid. Rosacea can be treated with antibiotics, sulfur, sodium sulfacetamide, and retinoids. The present invention relates to a device that can be used to treat acne or rosacea, or other conditions that affect barrier membranes.

SUMMARY OF THE INVENTION

In one aspect, the present invention features a device having a barrier membrane contacting surface, the device containing: a power source; a first conductive electrode; a second conductive electrode; and a carrier; wherein the power source is in electric communication with the first conductive electrode and the second conductive electrode, wherein the first conductive electrode and the second conductive electrode are in ionic communication with the carrier, and wherein the carrier is in communication with the barrier membrane contacting surface. In another aspect, the present invention features a method of administering electricity to a human barrier membrane by applying to the membrane such a device. In another aspect, the present invention features a method of treating a skin condition by applying to the skin such a device.

In another aspect, the present invention features a device having a barrier membrane contacting surface, the device containing: a power source; a first conductive electrode; a second conductive electrode; and a carrier containing an active agent; wherein the power source is in electric communication with the first conductive electrode and the second conductive electrode, wherein the first conductive electrode and the second conductive electrode are in ionic communication with the carrier, and wherein the carrier is in communication with the barrier membrane contacting surface. In another aspect, the present invention features a method of administering electricity to a human barrier membrane by applying to the membrane such a device. In another aspect, the present invention features a method of treating a skin condition by applying to the skin such a device.

In another aspect, the present invention features a device having a barrier membrane contacting surface, the device containing: a power source; a first conductive electrode; a second conductive electrode; a first light emitting diode; and a carrier containing an active agent; wherein the power source is in electric communication with the first conductive electrode, the second conductive electrode, and the light emitting diode, and wherein the device is arranged such that light from the first light emitting diode and the carrier are in communication with the barrier membrane contacting surface. In another aspect, the present invention features a method of administering an active agent to a human barrier membrane by applying to the membrane such a device. In another aspect, the present invention features a method of treating a skin condition by applying to the skin such a device.

In another aspect, the present invention features a method of treating a skin condition by applying to the skin a device having a barrier membrane contacting surface that administers an oxidizing agent to the barrier membrane, wherein the device contains: a power source; a first conductive electrode, wherein the first conductive electrode is an inert anode; a second conductive electrode, wherein the second conductive electrode is a cathode; and a carrier containing water; wherein the power source is in electric communication with the first conductive electrode and the second conductive electrode, wherein the first conductive electrode is in ionic communication with the carrier, wherein the oxidizing agent is generated by electric current passing from the first conductive electrode through the carrier, and wherein the carrier is in communication with the barrier membrane contacting surface. In another aspect, the present invention features a method of administering an oxidizing agent to a barrier membrane by applying to the membrane such a device.

In another aspect, the present invention features a method of treating a skin condition by applying to the skin a device having a barrier membrane contacting surface that administers a reducing agent to the barrier membrane, wherein the device contains: a power source; a first conductive electrode, wherein the first conductive electrode is an inert cathode; a second conductive electrode, wherein the second conductive electrode is a anode; and a carrier containing water; wherein the power source is in electric communication with the first conductive electrode and the second conductive electrode, wherein the first conductive electrode is in ionic communication with the carrier, wherein the reducing agent is generated by electric current passing from the first conductive electrode through the carrier, and wherein the carrier is in communication with the barrier membrane contacting surface. In another aspect, the present invention features a method of administering an reducing agent to a barrier membrane by applying to the membrane such a device.

DETAILED DESCRIPTION OF THE INVENTION

Figure 1:
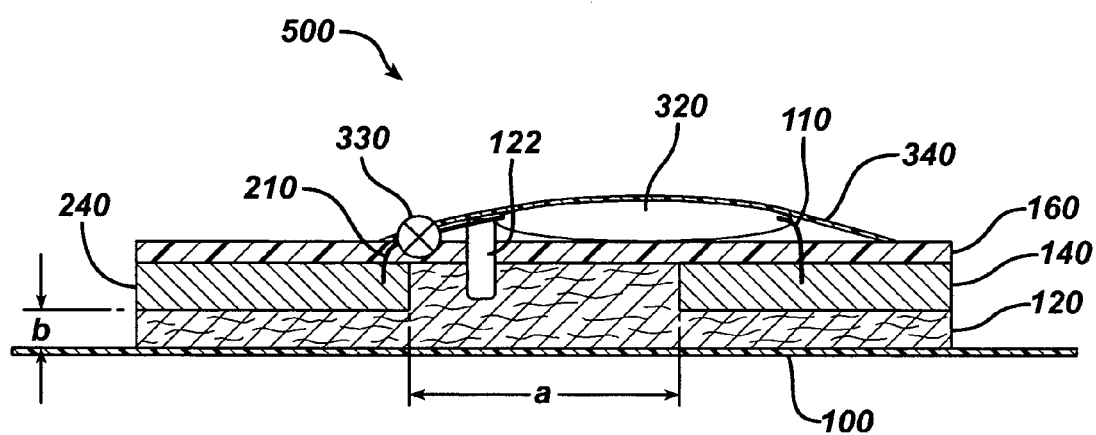
FIG. 1 is a cross-sectional view of one embodiment of the device suitable for practicing the invention. The battery 320 is located at the back of the device 500.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., %(W/W)).

What is meant by a "product" is a product containing the device in finished packaged form. In one embodiment, the product contains instructions directing the user to apply the device to the barrier membrane (e.g., to treat a skin condition). Such instructions may be printed on the device, label insert, or on any additional packaging.

In one aspect, the present invention features promoting a device of the present invention for its intended use. What is meant by "promoting" is promoting, advertising, or marketing. Examples of promoting include, but are not limited to, written, visual, or verbal statements made on the product or in stores, magazines, newspaper, radio, television, internet, and the like.

As used herein, "pharmaceutically-acceptable" means that the ingredients which the term describes are suitable for use in contact with the barrier membrane (e.g., the skin or mucosa) without undue toxicity, incompatibility, instability, irritation, allergic response, and the like.

As used herein, "safe and effective amount" means an amount of the ingredient or of the composition sufficient to provide the desired benefit at a desired level, but low enough to avoid serious side effects. The safe and effective amount of the ingredient or composition will vary with the area being treated, the age and skin type of the end user, the duration and nature of the treatment, the specific ingredient or composition employed, the particular cosmetically-acceptable carrier utilized, and like factors.

As used herein, the term "treatment" means the treatment (e.g., alleviation or elimination of symptoms and/or cure) and/or prevention or inhibition of the condition (e.g., a skin condition). What is meant by a "skin condition" is a dermatological disease or disorder (including, but not limited to, acne, rosacea, or skin infections) or skin characteristic (including, but not limited to, pigmentation, hair growth regulation, skin texture, skin firmness, skin elasticity, skin vasculature, dark circles, cellulite, sebum regulation, and skin shine).

The present invention relates to a device for the delivery of electricity (e.g., to induce a desirable biological response) and/or an active agent into a barrier membrane. In one embodiment, the device of the present invention is a self-contained device containing a battery as power source and two conductive electrodes in electric communication with the positive and negative poles of the battery. By "electric communication" is meant that electrons can pass between the elements of the device (e.g., between the power source and an conductive electrode of the device).

In one embodiment, the two conductive electrodes are in ionic communication with the carrier containing an electrolyte. By "ionic communication" it meant that ions of one or more electrolytes in the carrier are in contact with the conductive electrode. This electrode configuration differs from those in conventional iontophoresis devices in which each conductive electrode is in contact with a separate carrier (e.g., each electrode is contained in a separate compartment and affixed to the skin with electric insulation between them in order that all the electric current travels through the skin to complete the electric circuit). An advantage of such an embodiment of the present invention includes the capability of delivering simultaneously active agents of opposite charges from the same carrier into substantially the same skin site under the conductive electrodes.

The device contains a barrier membrane contacting surface. The device is arranged such that carrier is in communication with the barrier membrane contacting surface (e.g., such that electricity and/or the active agent may be administered from the carrier into the barrier membrane). In one embodiment, the carrier is the barrier membrane contacting surface (e.g., the carrier is a hydrogel). In one embodiment, the device contains a light emitting diode such that light from the light emitting diode is in communication with the barrier membrane contacting surface (e.g., such that the light may be administered to the barrier membrane).

In one embodiment, the device of the present invention delivers an active agent into the barrier membrane. The active agents to be delivered by the device of the present invention include active agents either initially incorporated in the carrier or electrochemically generated by the electric current passing from a conductive electrode through the carrier during use.

Power Source

The power source may be conventional direct current (DC) or pulsed DC, such as that disclosed in U.S. Pat. No. 5,042,975. In one embodiment, the current density to be used by the device in the present invention (current intensity per unit area of the barrier membrane) is generally less than about 0.5 mA/cm$^2$, such as less than about 0.1 mA/cm$^2$ or less than about 0.05 mA/cm$^2$. In one embodiment, the power source produces a voltage of from about 0.1 volts to about 9 volts, such as from about 1 to about 3 volts, such as about 1.5 volts.

In one embodiment, the power source is a battery (e.g., a rechargeable or disposable battery). In one embodiment, the battery is a disposable battery of small size suitable for a wearable patch or facial mask type adhesive device. Examples of suitable batteries include, but not limited to, button or coin batteries such as silver oxide, lithium, and zinc air batteries (which are typically used in small electronic devices). A zinc air battery is preferred because of its small size and high energy density, as well as its environmental friendliness. Examples of zinc air batteries include, but are not limited to, Energizer™ AC5 and AC10/230 (Eveready Battery Co. Inc., St. Louis, Mo.). Another preferred battery for the device is a flexible thin layer open liquid state electrochemical cell battery, such as a battery described in U.S. Pat. No. 5,897,522.

Carrier

The carrier of the present invention is a liquid (e.g., a solution, a suspension, or an emulsion which may be immobilized within an absorbent material such as gauze or non-woven pad), a semi-solid (e.g., a gel, a cream, a lotion, microemulsion, or hydrogel), or a solid (e.g., a lyophilized composition which may be reconstituted by adding a liquid prior to use) that during use is capable of conducting electricity from a conducting electrode (e.g., the carrier contains one or more electrolytes and water).

Examples of electrolytes include, but are not limited to, pharmaceutically acceptable organic and organic salts and buffers. Examples of salts include, but are not limited to, chloride salts (such as sodium chloride, potassium chloride, lithium chloride, calcium chloride, strontium chloride, magnesium chloride or other chloride salts), as well as salts of sodium, potassium, lithium, calcium, magnesium, strontium, fluoride, iodide, bromide. Examples of buffers include, but are not limited to, phosphates, citrates, acetates, lactates, and borates In one embodiment, the electrolyte is an active agent, or becomes an active agent after the passage of the electric current through the carrier. Examples of such electrolyte-active agents include, but are not limited to, salicylic acid, salicylates, and other weak acid or weak base active agents.

In one embodiment, the carrier contains water. In a further embodiment, the carrier may also contains one or more organic solvents. Examples of organic solvents include, but are not limited to: dimethyl isosorbide; isopropylmyristate; surfactants of cationic, anionic and nonionic nature; vegetable oils; mineral oils; waxes; gums; synthetic and natural gelling agents; alkanols; glycols; and polyols.

Examples of glycols include, but are not limited to, glycerin, propylene glycol, butylene glycol, pentalene glycol, hexylene glycol, polyethylene glycol, polypropylene glycol, diethylene glycol, triethylene glycol, glycerol, and hexanetriol, and copolymers or mixtures thereof. Examples of alkanols include, but are not limited to, those having from about 2 carbon atoms to about 12 carbon atoms (e.g., from about 2 carbon atoms to about 4 carbon atoms), such as isopropanol and ethanol. Examples of polyols include, but are not limited to, those having from about 2 carbon atoms to about 15 carbon atoms (e.g., from about 2 carbon atoms to about 10 carbon atoms) such as propylene glycol.

The organic solvents may be present in the carrier in an amount, based upon the total weight of the carrier, of from about 1 percent to about 90 percent (e.g., from about 5 percent to about 50 percent). Water may be present in the carrier (prior to use) in an amount, based upon the total weight of the carrier, of from about 5 percent to about 95 percent (e.g., from about 50 percent to about 90 percent).

The carrier may also contain: preservatives (such as cresol, chlorocresol, benzyl alcohol, methyl p-hydroxylbenzoate, propyl p-hydroxybenzoate, phenol, thimerosal, benzalkonium chloride, benzethonium chloride, and phenylmercuric nitrate); stabilizing agents or antioxidants (such as ascorbic acid, ascorbic acid esters, butylhydroxy anisole, butylhydroxy toluene, cysteine, N-acetylcysteine, sodium bisulfite, sodium metabisulfite, sodium formaldehydesulfoxylate, acetone sodium bisulfite, tocopherols, and nordihydroguaiaretic acid); chelating agents (such as ethylenediaminetetraacetic acid and its salts); buffers (such as acetic acid, citric acid, phosphoric acid, glutamic acid, and salts thereof); and tonicity adjusting agents (such as sodium chloride, sodium sulfate, dextrose and glycerin).

In one embodiment, the carrier may also contain a suspending material and/or a fluid-absorbing material (e.g., for physically stabilizing the ingredients of the carrier). Examples of suspending materials include, but are not limited to: cotton-based gauze; non-woven pads made of rayon or a mixture of rayon, polyester and/or other polymer fibers; open-cell foam and sponge-like materials contained of polyurethane, polyester and/or other polymers; and cross-linked and noncross-linked gelling materials, such as polyacrylamide, polyvinyl alcohol, gelatin, hydroxymethylcellulose, hydroxyethylcellulose, hydroxypropylcellulose, methylcellulose, and carboxymethylcellulose.

Examples of fluid-absorbing material include, but are not limited to: cross-linked and non-cross-linked polymers; swellable polymers such as water-swollen cellulose derivatives (e.g., methylcellulose (MC), hydroxyethyl methylcellulose (HEMA), hydroxypropyl methylcellulose (HPMC), ethylhydroxyethyl cellulose (EHEC), hydroxyethylcellulose (HEC), hydroxypropylcellulose (HPC), and carboxymethylcellulose (CMC) and their salts); polyvinyl alcohol (PVA); polyvinylpyrrolidone (PVP); polyethylene oxide (PEO); polymers prepared by monomers such as hydroxyethyl methacrylate (HEMA), hydroxyethoxyethyl emthacrylate (HEEMA), hydroxydiethoxyethl methacrylate (HDEEMA), methyoxyethyl methacrylate (MEMA), methoxyethoxyethyl methacrylate (MEEMA), methyldiethoxyethyl methacrylate (MDEEMA), ethylene glycol dimethacrylate (EGDMA), n-vinyl-2pyrrolidone (NVP), methacrylic acid (MA), and vinyl acetate (VAC); polycrylamide; gelatin; gums and polysaccharides such as gum arabic, gum karaya, gum tragacanth, guar gum, gum benzoin, and alginic acid and their salts; polyethylene glycol (PEG); polypropylene glycol (PPG); and clays or other swellable minerals such as bentonite and montmorillonite. The amount of fluid absorbable material in the carrier may range from about 0.1% to about 95%, by weight, such as from about 1% to about 20%, by weight, of the carrier.

Another embodiment of the present invention is directed to pairing one or more inert conductive electrodes in order to electrochemically generate oxidizing or reducing agents from electrochemically reactive materials in situ in the carrier. Such oxidizing or reducing agents can be used as active agents to treat barrier membrane conditions.

Examples of the electrochemically reactive materials in the carrier according to the present invention include, but are not limited to, water and compounds containing the elements selected from the Periodic Table of the Elements VIIB and VIIB (such as oxygen, sulfur, fluorine, chlorine, bromine, and iodine).

In one embodiment, the reactive material reacts with the inert anode to form an oxidizing agent. Examples of such a reactive material includes, but is not limited to, the ions $OH^-$, $Cl^-$, $I^-$, $Br^-$, $SO_3^{2-}$, and $HCO_3^-$. The present device, thus, enables to generation of oxidizing agents, such as nascent oxygen (e.g., singlet oxygen), chlorine and chlorine dioxide gases, which are difficult to formulate in a conventional topical product.

In one embodiment, the reactive material reacts with the inert cathode to form a reducing agent. Examples of such a reactive material includes, but is not limited to, oxidized or disulfide forms of thio-compounds with one or more sulfhydryl functional groups, thio-containing amino acids and their salts or esters, and sulfides. Examples of such thio-compounds include, but are not limited to: thioglycolic acid and its salts, such as thioglycolates of calcium, sodium, strontium, potassium, ammonium, lithium, magnesium, and other metal salts; thioethylene glycol; thioglycerol; thioethanol; thioactic acid; and thiosalicylic acid; and their salts. Examples of the thio-containing amino acids include, but are not limited to, L-cysteine, D-cysteine, DL-cysteine, N-acetyl-L-cysteine, DL-homocysteine, L-cysteine methyl ester, L-cysteine ethyl ester, N-carbamoyl cysteine, glutathione, and cysteamine. Examples of sulfides, include but are not limited to, calcium, sodium, potassium, lithium and strontium sulfides and glutathione disulfide. The inert cathode converts the aforementioned reactive oxidized or disulfide form of a sulfur-containing compound to a thio-containing compound, or a sulfydryl-containing compound. Examples of such a conversion is the conversion of cystine to cysteine and the conversion of the oxidized form of glutathione to glutathione.

In one embodiment, the concentration of the reactive material in the carrier may range from about 0.01% to about 25%, by weight, such as from about 0.1% to about 10%, by weight, of the carrier. The pH value of the carrier may range from about pH 1.5 to about pH 9, preferably from pH 2 to pH 7, and most preferably from about pH 3 to pH 5.

In one embodiment, the carrier contains an adhesive. The adhesive is used to affix the device to the barrier membrane. Examples of hydrophobic adhesives include, but are not limited to, silicones, polyisobutylenes and derivatives thereof, acrylics, natural rubbers, and combinations thereof. Examples of silicone adhesives include, but are not limited to, Dow Corning 355 available from Dow Corning of Midland, Mich.; Dow Corningo X7-2920; Dow Corning X7-2960; and GE 6574 available from General Electric Company of Waterford, N.Y. Examples of acrylic adhesives include, but are not limited to, vinyl (D acetate-acrylate) multipolymers such as Gelva 7371, available from Monsanto Company of St. Louis, Mo.; Gelvao 7881; Gelva 2943; and 1-780 medical grade adhesive available from Avery Dennison of Painesville, Ohio. Examples of hydrophilic adhesives include, but are not limited to, gum papaya and other natural gums, MC, HEMA, HPMC, EHEC, HEC, HPC, CMC, PAV, PVP, PEO, HEMA, HEEMA, HDEEMA, MEMA, MEEMA, MDEEMA, EGDMA, NVP MA, VAC, polycrylamide. getatins, gum arabic, gum karaya, gum tragacanth, guar gum, gum benzoin, and alginic acid and their salts, polyethylene glycol (PEG), and polypropylene glycol (PPG).

In one embodiment, the concentration of the adhesive in the carrier may range from about 0.1% to about 95%, by weight, such as from about 1% to about 20%, by weight, of the carrier.

Electrodes

The conductive electrodes of the present invention may be a reactive conductive electrodes or inert conductive electrodes. What is meant by a "reactive conductive electrode" is that the conductive electrode itself goes through a change in its chemical composition during the electrode chemical reactions occurring with the electric current passing through the electrode during the process. In one embodiment, the reactive conductive electrode is made of reactive materials such as metal halides (e.g., silver-silver chloride (Ag/AgCl), silver-silver bromide, and silver-silver iodide). In this case, the primary electrochemical reaction at the cathode surface is conversion of solid silver halide to metallic silver with little unwanted consumption of the oxidizing agents generated by the anode. The released halide ions may be subsequently oxidized to oxidizing agents, such as chloride ions to chlorine ($Cl_2$), hypochlorous acid (HClO), and hypochlorite ions ($ClO^-$), and iodide ions to iodine.

What is meant by an "inert conductive electrode" is that the conductive electrode itself does not go through a change in its chemical composition. In one embodiment, the anode is made of an inert conductive electrode, so that the electrochemical process at the surface of the anode generates oxidizing agents such as nascent oxygen (e.g., by electrolysis of water) and/or chlorine-containing oxidizing agents such as chlorine, hypochlorite, chlorate and perchlorate, and chlorine dioxide. Nascent oxygen is an oxidizing agent that is inhibitive to *P. acnes*, and chlorine-containing oxidizing agents are potent antimicrobial agent with bacteriacidal activity.

In one embodiment, the inert conductive electrode is made of, or coated on the surface with, an inert materials such as noble metals (e.g., gold, platinum, or gold-coated conductive metals), conductive carbon (e.g., glassy carbon or graphite), carbon-embedded polymers (e.g., carbon silicone rubbers), conductive carbon polymer foam or sponge, silver halide-coated silver (e.g., silver chloride-coated silver, silver bromide-coated silver, and silver iodide-coated silver), and corrosive resistant alloys.

Active Agents

In one embodiment, the carrier contains one or more active agents. What is meant by an "active agent" is a compound (e.g., a synthetic compound or a compound isolated from a natural source) that has a cosmetic or therapeutic effect on the barrier membrane.

In one embodiment, the carrier contains an anti-acne and/or anti-rosacea agent. Examples of anti-acne and anti-rosacea agents include, but are not limited to: retinoids such as tretinoin, isotretinoin, motretinide, adapalene, tazarotene, azelaic acid, and retinol; salicylic acid; benzoyl peroxide; resorcinol; sulfur; sulfacetamide; urea; antibiotics such as tetracycline, metronidazole, and erythromycin; anti-inflammatory agents such as corticosteroids (e.g., hydrocortisone), ibuprofen, naproxen, and hetprofen; and imidazoles such as ketoconazole and elubiol; and salts, esters, and other derivatives thereof. Other examples of anti-acne active agents include essential oils, alpha-bisabolol, dipotassium glycyrrhizinate, camphor, □-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and other valences, synthetic phospholipids and natural phospholipids such as Arlasilk™ phospholipids CDM, SV, EFA, PLN, and GLA (Uniqema, ICI Group of Companies, Wilton, UK).

In one embodiment, the device of the present invention contains an anti-aging agent. Examples of suitable anti-aging agents include, but are not limited to: inorganic sunscreens such as titanium dioxide and zinc oxide; organic sunscreens such as octyl-methoxy cinnamates; retinoids; vitamins such as vitamin E, vitamin A, vitamin C, and vitamin B and vitamin salts or derivatives such as ascorbic acid di-glucoside and vitamin E acetate or palmitate; alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methylpyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts, esters, and other derivatives thereof.

In one embodiment, the carrier contains a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacin and vitamin C; azelaic acid; linolenic acid and linoleic acid; placertia; licorice; and extracts such as chamomile and green tea; and salts, esters, and other derivatives thereof.

In one embodiment, the carrier contains a plant extract. Examples of plant extracts include, but are not limited to, feverfew, soy, glycine soja, oatmeal., what, aloe vera, cranberry,hazel witch, alnus, arnica, artemisia capillaris, asiasarum root, birrh, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural or synthetic isoflavonoids, soy isoflavones, natural or synthetic essential oils.

In one embodiment, the carrier contains metals such as metal ions or fine powders. Examples of such metals include, but are not limited to, gold, silver, copper, zinc.

Other active agents include those commonly used as for topical treatment and in cosmetic treatment of skin tissues, such as topical antibiotics for wounds, topical antifungal drugs to treat fungal infections of the skin and nails, and antipsoriatic drugs to treat psoriatic lesions of the skin and psoriatic nails.

Examples of antifungal drugs include but are not limited to miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts. In one embodiment, the antifungal drugs are an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline—10 hydrochloride and tetrachcycline hydrochoride), clindamycin phsphate, gentamicin sulfate, metronidazole, hexylresorcinol, methylbenzethonium chloride, phenol, quaternary ammonium compounds, tea tree oil, and their pharmaceutically acceptable salts.

Examples of antimicrobials include but are not limited to salts of chlorhexidine, such as Iodopropynyl butylcarbamate, diazolidinyl urea, chlorhexidene digluconate, chlorhexidene acetate, chlorhexidene isethionate, and chlorhexidene hydrochloride. Other cationic antimicrobials may also be used, such as benzalkonium chloride, benzethonium chloride, triclocarbon, polyhexamethylene biguanide, cetylpyridium chloride, methyl and benzothonium chloride. Other antimicrobials include, but are not limited to: halogenated phenolic compounds, such as 2,4,4',-trichloro-2-hydroxy diphenyl ether (Triclosan); parachlorometa xylenol (PCMX); and short chain alcohols, such as ethanol, propanol, and the like. In one embodiment, the alcohol is preferably at a low concentration (e.g., less than about 10% by weight of the carrier, such as less than 5% by weight of the carrier) so that it does not cause undue drying of the barrier membrane.

Examples of antipsoriatic drugs or drugs for seborrheic dermatitis treatment include, but are not limited to, corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts, esters, and other derivatives thereof. Examples of anti-viral agent, include, but are not limited to, imiquimod and its derivatives, podofilox, podophyllin, interferon alpha, acyclovir, famcyclovir, valcyclovir, reticulos and cidofovir.

Examples of anti-inflammatory agent, include, but are not limited to, suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, betamethasone dipropionate, and triamcinolone. The preferred steroidal anti-inflammatory for use in the present invention is hydrocortisone. A second class of anti-inflammatory agents which is useful in the compositions of the present invention includes the nonsteroidal anti-inflammatory agents.

Other active agents include, but are not limited to, wound healing enhancing agent, scar reducing agents, analgesic agents, anesthetics, hair growth enhancing agents such as minoxadil, antihypertensives, drugs to treat coronary artery diseases, anticancer agents, endocrine and metabolic medication, neurologic medications, medication for cessation of chemical additions, motion sickness, and protein and peptide drugs.

The amount of the active agent in the carrier will depend on the active agent and/or the intended use of the device. In one embodiment, the carrier contains a safe and effective amount of the active agent, for example, from about 0.001 percent to about 20 percent, by weight, such as from about 0.01 percent to about 5 percent, by weight, of the carrier.

Light Emitting Diode

In one embodiment, the device contains one or more light emitting diodes. Light emitting diodes (LEDs) of certain spectrum may be incorporated into the device to emit light to the barrier membrane (e.g., to treat skin conditions such as acne and rosacea). The light emitting diode may also provide a signal to the user indicating that the device is operating properly.

The spectrum of the LED's according to the current invention may range from about 300 nm to about 1500 nm, such as from about 350 nm to about 1000 nm. In one embodiment, the range of the LED includes violet-blue, green, red, and infrared ranges, e.g., from about 400 nm to about 450 nm such as from about 407 nm to about 420 nm; from about 510 nm to about 550 nm; from about 600 nm to about 700 nm; and from about 1300 nm to about 1500 nm. In one embodiment, the device contains two LEDs, one that emits light having a wavelength of from about 400 nm to about 500 nm and one which emits light from about 700 nm to about 1000 nm.

Photosensitizer agents, such as 5-aminolaevulinic acid (ALA), hypericin, St. John's wort powder or extract, or other synthetic or natural photosensitizer agents, may be incorporated into the carrier as active agents to be delivered and irradiated by the device with LED's of the present invention. The light irradiation from the LED's, together with the photosensitizer agent(s) and other aforementioned active agents, electrochemically generated oxidizing agents (e.g., peroxides, nascent oxygen, chlorine dioxide, and chlorine), and/or electric stimulation of the barrier membrane may work synergistically to achieve an improved efficacy in treating membrane disorders such as acne and rosacea.

Use

In one embodiment, the device is used for the treatment of a barrier membrane condition (e.g., the delivery of an active agent, light, and/or electricity into the membrane such as the skin, vaginal, or rectal mucosa barrier membrane of a human). In one embodiment, the device is used for the treatment of skin conditions. Examples of such treatments include, but are not limited to: treatment of acne, rosacea, or other microbial infections of the skin; reduction the visible signs of skin aging (e.g., wrinkles, sagging, and age-spots); folliculitis and pseudo-folliculitis barbae; treatment of wounds and lesions (e.g., enhancing healing and scar reduction); sebum regulations (e.g., sebum reduction or oily/shining skin appearance inhibition or control); pigmentation regulation (e.g., reduction of hyperpigmentation or pigmentation of light skin); hair growth retardation (e.g., skin on the leg) or hair stimulation (e.g., scalp); and treatment of dermatitis (e.g., atopic, contact, or seborrheic dermatitis) and/or psoriasis.

In another embodiment, the device is used for the treatment of mucosal conditions. Examples of such treatments include, but are not limited to: treatment of vaginal candidiasis and vaginosis, genital herpes, and other microbial infections of the mucosa.

Another embodiment of the present invention is the device induces certain desirable biological responses that facilitate the treatment of the barrier membrane conditions. These desirable biological responses may be induced by the electric current passage through the barrier membrane, and/or the electrochemically generated oxidizing materials, together with the active agents delivered by iontophoresis from the carrier, in treating the barrier conditions. Examples of the desirable responses of the barrier membrane may include, but are not limited to, sebum regulation (e.g., reduction of sebaceous gland activity), inhibition of anaerobotic microbial growth and establishment of a healthier membrane microflora or (e.g, reduction of *P. acne* growth and of production of irritating fatty acids), blood vasoconstriction (thus promoting local accumulation of active agents or removal of dark circle under the eye due to deoxyhemoglobins), enhanced tissue immunological activity (e.g, increased elimination of pathogenic microbes on tissue's own defense systems), improved tissue repairing (e.g., enhanced healing and reduced scarring of lesions such as acne lesions), and improved keratolytic activity of the carrier (e.g., softening of keratin plugs of comedos in whiteheads and blackheads of acne, and facilitating their removal).

In another aspect, the invention also features the method of converting an active agent from a less active form to a more active form via oxidation or reduction via an inert electrode (e.g., cystine to cysteine, disulfide acetyl-cysteine to acetylcysteine, and retinol to retinoic acid). Thus, an unstable agent can be stored in a more stable form and converted to its active form prior to administration. In a further aspect, the generation of reducing agents by the device of the present invention can be used to stabilize oxygen-labile active agents. Examples of such oxygen-labile active agents include, but are not limited to, retinoids, ascorbic acid, and benzoyl peroxide.

Shape

The device may be fabricated into various shapes and sizes to fit the contours of various anatomical surfaces of the barrier membranes. For examples, it may be made as a whole facial mask with openings/holes to expose the eyes, eye bows, nose, and mouth; a partial facial mask covering only the upper or lower half of the face; or a patch covering only the forehead, or the under eye region, the chin and jaw region, the neck, the back, wound, acne lesion or pimple, or other specific area of a barrier membrane in need of treatment.

Devices

One embodiment of the present invention is represented schematically in FIG. 1. The device 500 contains a removable release liner 100, a carrier layer 120, a first conductive electrode 140, a second conductive electrode 240, electric lead wires 110 and 210 connecting the two poles of a battery 320 to the two oppositely charged conductive electrodes, an electric power switch 330 located on the lead wire 220, a light emitting diode (LED) 122, a backing layer 160 separating the carrier layer 120 from the battery 320, and a battery cover layer 340.

The gap "b" depicts the distance between two conductive electrodes 140 and 240 to the release liner (or the membrane following application of the device), and the gap "a" represents the distance between two oppositely charged conductive electrodes. In one embodiment, the ratio of gap "a" to gap "b" is at least about 1, such as at least about 2 or at least about 5.

The backing layer 160 may be impermeable to the active agent contained within the carrier layer 120, and is preferably not permeable to water or other solvents in the carrier layer 120. The battery 320 may be encased in an electric insulating, water-impermeable polymer layer (not shown in the figure). The backing layer 160 and the batter cover layer 340 may be made of flexible material that is impermeable to water, e.g., polymers such as polyethylene, polypropylene, polyvinyl acetate, polyurethane, silicone rubber, or polyvinyl chloride.

Optionally, there can be an electric circuit (not shown) in device 500 to provide a constant current located between the battery 320 and conductive electrode 140 and/or conductive electrode 240.

In a further embodiment, the backing layer 160 is permeable to electrochemically generated gases (e.g., oxygen, chlorine, and hydrogen) in order to limit excess accumulation of the gases in the carrier which can cause tissue irritation and/or undesirable deformation of the device.

The carrier layer 120 is an adhesive hydrogel containing the active agent. The active agent may be incorporated into the carrier layer 120 as dissolved molecules and ions, dispersed solid particles, or liquid droplets such as cream, lotion, emulsion, multi-emulsion, microemulsion, and/or liposome compositions. The carrier layer 120 may also contain a solid supporting matrix (e.g., a gauze, non-woven or sponge-like material).

A removable liner sheet 100 covers the carrier layer 120. The selection of the removable release-liner 100 is dependent on the type of the adhesive hydrogel used in carrier layer 120. The release liner sheet 100 is typically a polymer sheet or a paper or fabric coated with a polymer, which has weak adhesion toward the adhesive hydrogel layer 120, thereby allowing it to be easily removed from the carrier layer 120 prior to use without damaging the carrier layer 120. Examples of the polymers typically used for the release liner 100 are silicones and polyethylenes. Alternatively, a wax may be used in the place of the polymer to coat the release liner 100.

In addition to, or in lieu of, the use of an adhesive in the carrier layer 120, the device 500 may be fastened to the barrier membrane with an adhesive tape, an elastic band, a band with a buckle (similar to a leather watch band), or a Velcro® band.

Figure 2:
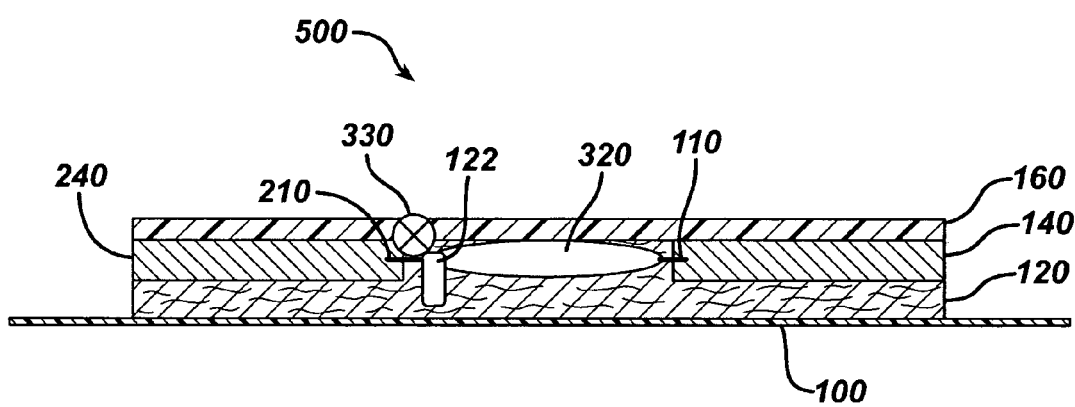
FIG. 2 is a cross-sectional view of one embodiment in accordance with the invention. The battery 320 is embedded in the carrier layer 120 of the device 500.

In order to use device 500, the removable release liner sheet 100 is peeled off, and the carrier hydrogel layer 120 of the device 500 is affixed to a barrier membrane, such as the skin, vaginal, or rectal mucosa barrier membrane, of the user. The device may be directly affixed to the barrier membrane if the carrier layer 120 contains an adhesive hydrogel. An electric potential is applied across the conductive electrodes 140 and 240 by switching on the power switch 330. Another embodiment of the present invention is represented schematically in FIG. 2. The battery 320 is located within the carrier layer 120. The advantage of this battery arrangement includes reduced bulkiness, enhanced esthetics and user comfort.

Figure 3:
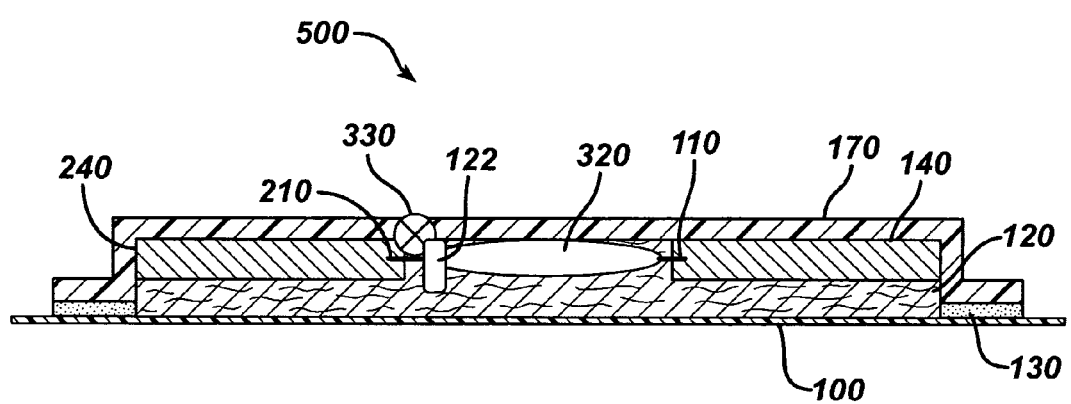
FIG. 3 is a cross-sectional view of one embodiment in accordance with the invention. The battery 320 is embedded in the carrier layer 120 that is enclosed in a chamber 160 with an opening affixed to the release liner 100 with an adhesive layer 130.

Another embodiment of the present invention is represented schematically in FIG. 3. Housing 170 contains an adhesive layer 130 coated onto the rim of the housing 170 for affixing device 500 to membrane during application. The housing 170 may be made of the same materials as the backing layer 160 described above. The adhesive in the adhesive layer 130 may be a polymeric, pressure sensitive and/or non-conductive. Suitable adhesive materials include, but are not limited to, silicones, polyisobutylenes and derivatives thereof, acrylics, natural rubbers, and combinations thereof.

Suitable silicone adhesives include, but are not limited to, Dow Corning 355 (available from Dow Corning of Midland, Mich.); Dow Corning X7-2920; Dow Corning 0 X7-2960; GE 6574 (available from General Electric Company of Waterford, N.Y.); and silicone pressure sensitive adhesives. Suitable acrylic adhesives include, but are not limited to, vinyl acetate-acrylate multipolymers, including, such as Gelva-7371 (available from Monsanto Company of St. Louis, Mo.); Gelva T 7881; Gelvac 2943; 1-780 medical grade adhesive available from Avery Dennison of Painesville, Ohio; and acrylic pressure sensitive adhesives.

When a zinc air battery is used as the power source of the device 500, the battery 320 is constructed in such a way that the orifice on the stainless steel cover is facing the opposite side of the carrier layer 120. An orifice is made on the battery cover layer to expose the orifice on the zinc air battery that is covered by a removable oxygen-impermeable cover. In this case, the power switch 230 is replaced by the removable oxygen-impermeable cover. The removable oxygen-impermeable cover can be used to begin (by removing it) or to halt the electrotransport process of the device (by re-covering the orifice).

In one embodiment, the carrier layer 120 contains at least two active agents carrying opposite electric charges. One example of such a composition is a composition containing from about 0.5 to about 2% salicylic acid and from about 0.01 to about 0.2% of a cationic quaternary ammonium antimicrobial agents (such as benzalkonium chloride, benzethonium chloride, methyl benzethonium chloride, and cetylpyridinium chloride), phenol, and/or chlorhexidine gluconate. The device 500 of the present invention can simultaneously deliver both active agents of opposite charges into the membrane.

The backing layer 160 may have some gas permeability, so called "breathable backing". The examples of such "breathable backing" material include, but are not limited to, a cotton or synthetic woven and nonwoven fabric layer, such as those fabric materials commonly used for bandages and sports bandages.

The lighting portion of the LED 122 is preferable located in the carrier layer 120 in close proximity to the skin. Locating the light source in the carrier layer 120 affixed to the barrier membrane has an advantage of minimizing the loss of light energy from reflection of skin surface. In addition, a light reflective layer may be used as the backing layer 160 (e.g., metalized polymer film) to further enhance the efficacy of phototherapy, and to achieve more homogeneous irradiation. The backing layer 160 may optionally be perforated as certain spots to make the light visible to the user to serve as an indicator that the device is working normally.

Figure 4:
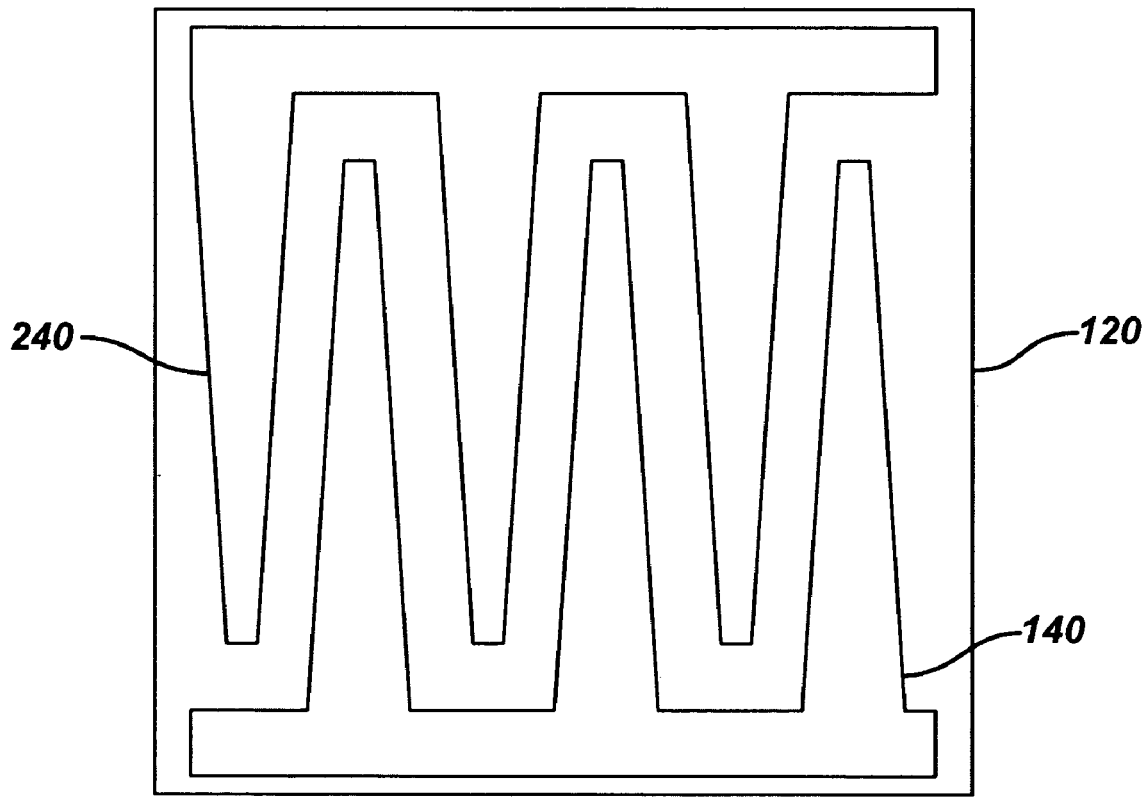
FIG. 4 is a top view of one embodiment in accordance with the invention showing the conductive electrodes 140 and 240 and carrier layer 120.
Figure 5:
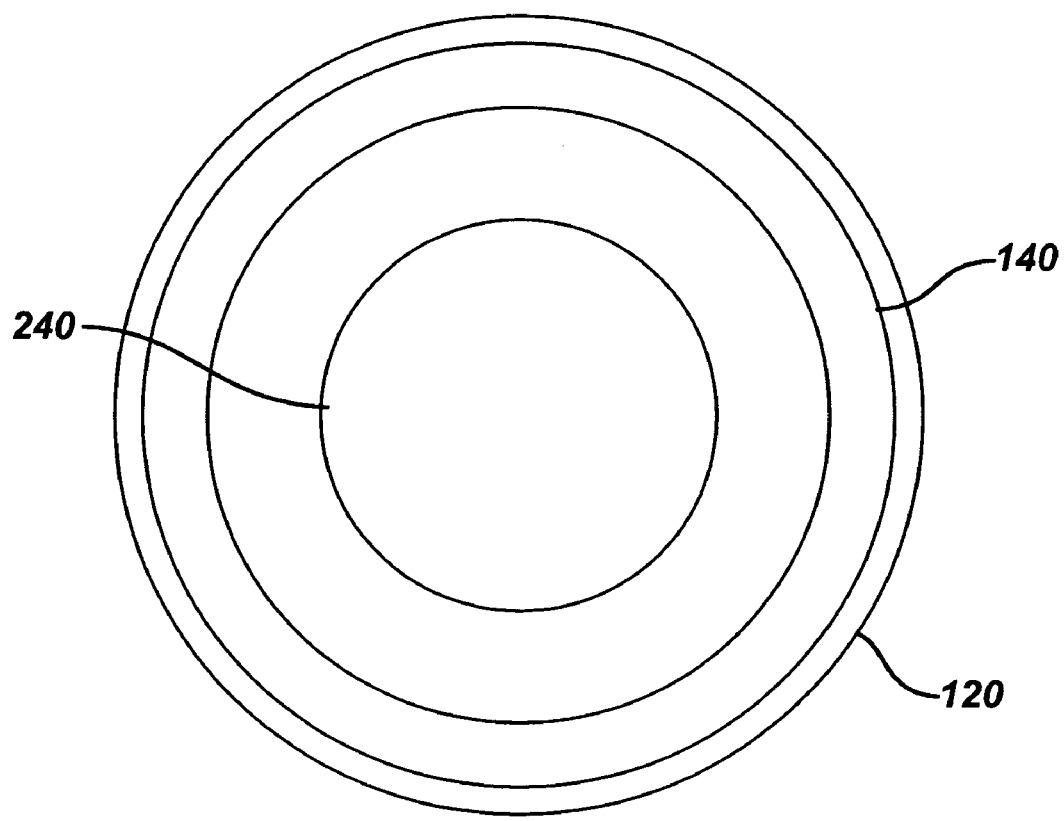
FIG. 5 is a top view of one embodiment in accordance with the invention showing the conductive electrodes 140 and 240 and carrier layer 120.

FIGS. 4 and 5 disclose one embodiment of the two different configurations of conductive electrode 140 and 240 in carrier layer 120.

Figure 6:
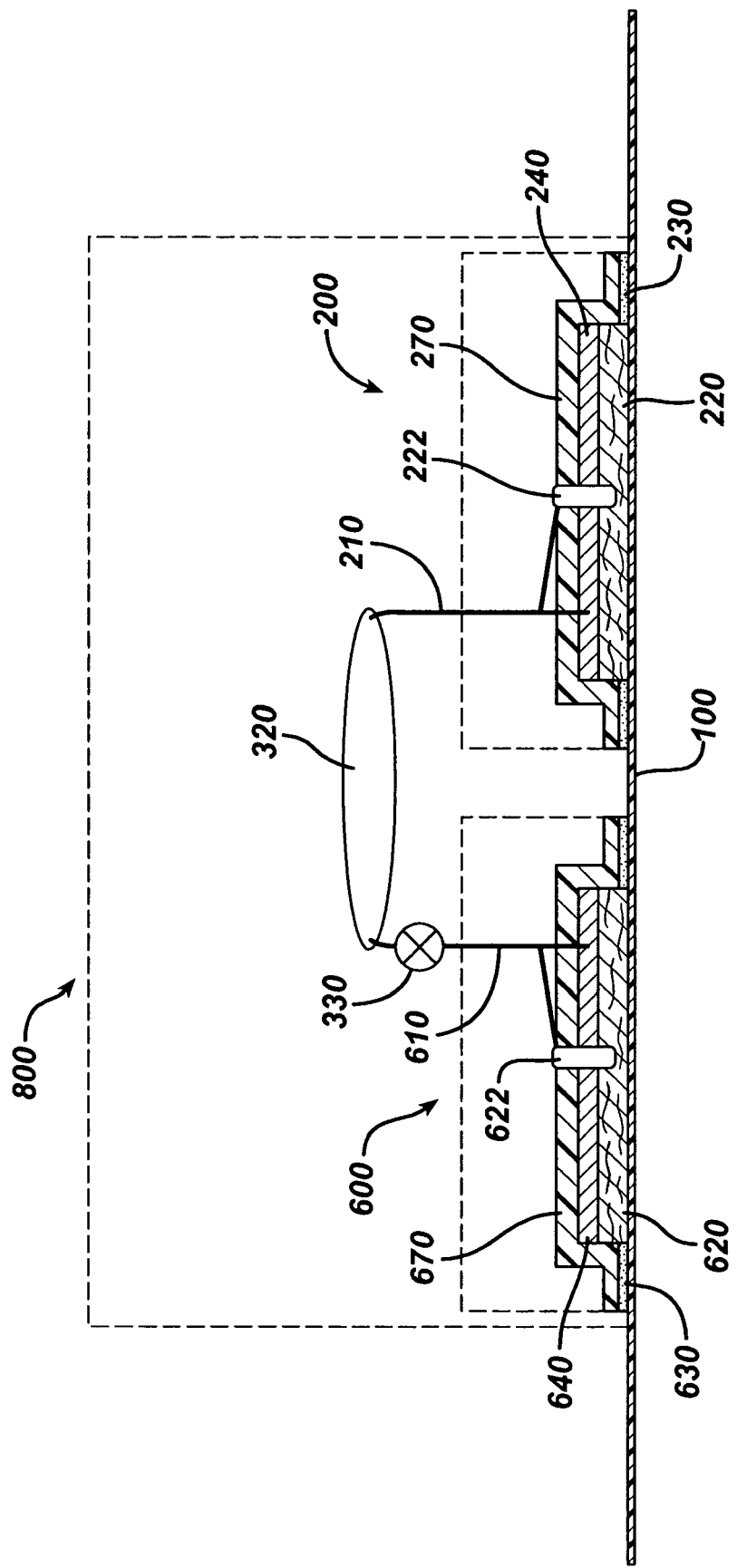
FIG. 6 is a cross-sectional view of one embodiment in accordance with the invention. The device 800 contains two electrode assemblies 200 and 600.

Another embodiment of the present invention is represented schematically in FIG. 6. The electrotransport device 800 containes two electrode assemblies 200 and 600, respective adhesive layers 230 and 630, respective carrier layers 220 and 620, respective conductive electrodes 240 and 640, respective light emitting diodes 222 and 622, respective housings 270 and 670, respective electric leads 210 and 610, battery 320 and electric switch 330. Similar to the aforementioned typical iontophoresis device, the two electrode assemblies 200 and 600 are to be affixed to the barrier membrane with an electric insulation between them, after the release liner 100 is removed prior to use.

EXAMPLES

Examples of several carriers, including the weight percentage range of the ingredients of such carriers, are set forth in Table 1.

TABLE 1

| Component | Percent by Weight of the Carrier | | | | | |
|---|---|---|---|---|---|---|
| | No. 1 | No. 2 | No. 3 | No. 4 | No. 5 | No. 6 |
| Salicylic acid | 0.1–10 | 2 | 2 | 0 | 0 | 0.1–10 |
| Benzyl peroxide | 0 | 0 | 0 | 0.5–10 | 0 | 0 |
| Sulfur | 0 | 0 | 0 | 0 | 3 | 3 |
| Resorcinol | 0 | 0 | 0 | 1 | 1 | 1 |
| Benzalkonium chloride | 0–2 | 0.1 | 0.1 | 0–2 | 0–2 | 0–2 |
| Benzethonium or methylbezethonium chloride | 0–2 | 0 | 0 | 0–2 | 0–2 | 0–2 |
| Cetylpyridium chloride | 0–2 | 0.1 | 0.1 | 0–2 | 0–2 | 0–2 |
| Phospholipid CDM | 0–40 | 5 | 5 | 0–40 | 0–40 | 0–40 |
| Hydrogen peroxide | 0–30 | 0 | 3 | 0–30 | 0–30 | 0–30 |
| Buffer (citrate, lactate, or phosphate salts of sodium, potassium, or lithium | 0–10 | 2 | 2 | 0–10 | 0–10 | 0–10 |
| Gelling agent (e.g., polyacrylates, cellulose, natural or synthetic gums, or polyacrylamide) | 0–20 | 5 | 5 | 0–20 | 0–20 | 0–20 |
| Chelating agent (e.g., EDTA) | 0–2 | 0.1 | 0.1 | 0–2 | 0–2 | 0–2 |
| Propylene glycol | 0–30 | 20 | 15 | 0–30 | 0–30 | 0–30 |
| Polyethylene glycol | 0–50 | 0 | 0 | 0–50 | 0–50 | 0–50 |
| Polypropylene glycol | 0–40 | 0 | 0 | 0–40 | 0–40 | 0–40 |
| Ethyl alcohol | 0–50 | 0 | 15 | 0–50 | 0–50 | 0–50 |
| Isopropyl alcohol | 0–50 | 0 | 0 | 0–50 | 0–50 | 0–50 |
| Dimethyl isosorbide | 0–20 | 2 | 0 | 0–20 | 0–20 | 0–20 |
| Isopropyl myristate | 0–30 | 1 | 1 | 0–30 | 0–30 | 0–30 |
| Purified water | Qs to 100 | Qs to 100 | Qs to 100 | Qs to 100 | Qs to 100 | Qs to 100 |

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A device having a barrier membrane contacting surface, said device comprising:
    a power source that produces conventional direct current;
    a first conductive electrode that is an anode;
    a second conductive electrode that is a cathode; and
    a carrier;
wherein said power source is in electric communication with said first conductive electrode and said second conductive electrode, wherein said first conductive electrode and said second conductive electrode are in ionic communication with said carrier, wherein said carrier is in communication with said barrier membrane contacting surface, and wherein said device is adapted to be affixed to said barrier membrane and to deliver electric current from said first conductive electrode, through said carrier, through said barrier membrane, and through said carrier to said second conductive electrode.

2. A device of claim 1, wherein said device comprises a housing and said first conductive electrode, said second conductive electrode, and said carrier are within said housing.

3. A device of claim 1, wherein said carrier is a semi-solid.

4. A device of claim 2, wherein said housing comprises an adhesive.

5. A device of claim 3, wherein said carrier comprises an adhesive.

6. A device of claim 1, wherein the ratio of the distance between the first conductive electrode and the second conductive electrode and the distance between the first conductive electrode and the barrier membrane contacting surface is at least about 1.

7. A device of claim 3, wherein the ratio of the distance between the first conductive electrode and the second conductive electrode and the distance between the first conductive electrode and the barrier membrane contacting surface is at least about 5.

8. A device of claim 1, wherein said power source produces a voltage from about 0.1 to about 3 volts.

9. A device of claim 1, wherein said power source produces a current density of less than about 0.5 mA/cm$^2$.

10. A device of claim 8, wherein said power source produces a current density of less than about 0.5 mA/cm$^2$.

11. A method of administering electricity to a human barrier membrane, said method comprising applying to said membrane a device having a barrier membrane contacting surface, said device comprising:

a power source that produces conventional direct current;

a first conductive electrode that is an anode;

a second conductive electrode that is a cathode; and a carrier;

wherein said power source is in electric communication with said first conductive electrode and said second conductive electrode, wherein said first conductive electrode and said second conductive electrode are in ionic communication with said carrier, wherein said carrier is in communication with said barrier membrane contacting surface, and wherein said device is adapted to be affixed to said barrier membrane and to deliver said electric current from said first conductive electrode, through said carrier, through said barrier membrane, and through said carrier to said second conductive electrode.

12. A method of claim 11, wherein the ratio of the distance between the first conductive electrode and the second conductive electrode and the distance between the first conductive electrode and the barrier membrane contacting surface is at least about 1.

13. A method of claim 11, wherein the ratio of the distance between the first conductive electrode and the second conductive electrode and the distance between the first conductive electrode and the barrier membrane contacting surface is at least about 5.

14. A method of claim 11, wherein said barrier membrane is skin.

15. A method of claim 14, wherein said skin comprises a wound.

16. A method of claim 11, wherein said barrier membrane is mucosa.

17. A method of claim 13, wherein said barrier membrane is skin.

18. A method of claim 17, wherein said skin comprises a wound.

19. A method of claim 13, wherein said barrier membrane is mucosa.

20. A method of treating a skin condition, said method comprising affixing to said skin in need of such treatment a device having a barrier membrane contacting surface, said device comprising:

a power source;

a first conductive electrode that is an anode;

a second conductive electrode that is a cathode; and a carrier;

wherein said power source is in electric communication with said first conductive electrode and said second conductive electrode, wherein said first conductive electrode and said second conductive electrode are in ionic communication with said carrier, and wherein said carrier is in communication with said barrier membrane contacting surface, and wherein said device is adapted to be affixed to said barrier membrane and to deliver electric current from said first conductive electrode, through said carrier, through said barrier membrane, and through said carrier to said second conductive electrode.

21. A method of claim 20, wherein said skin condition is acne or rosacea.

22. A method of claim 20, wherein said skin condition is a skin infection.

23. A method of claim 20, wherein said skin condition is excess sebum secretion.

24. A method of claim 20, wherein said skin condition is excess skin pigmentation.

25. A method of claim 20, wherein said skin condition is folliculitis or pseudo-folliculitis barbae.

26. A method of claim 20, wherein said skin condition is wrinkles, sagging skin, or age-spots.

* * * * *